(12) United States Patent
Olson et al.

(10) Patent No.: US 7,609,073 B2
(45) Date of Patent: Oct. 27, 2009

(54) METHODS AND DEVICES FOR MEASURING VOLUME RESISTIVITY

(75) Inventors: Jared K. Olson, Saratoga Springs, UT (US); Ronald G. Mellus, Erda, UT (US); Travis A. Bodrero, West Jordan, UT (US)

(73) Assignee: Alliant Techsystems Inc., Edina, MN (US)

( * ) Notice: Subject to any disclaimer, the term of this patent is extended or adjusted under 35 U.S.C. 154(b) by 169 days.

(21) Appl. No.: 11/438,084

(22) Filed: May 19, 2006

(65) Prior Publication Data

US 2007/0268027 A1 Nov. 22, 2007

(51) Int. Cl.
*G01R 27/08* (2006.01)
(52) U.S. Cl. ..................... 324/691; 324/722
(58) Field of Classification Search .............. 324/691
See application file for complete search history.

(56) References Cited

U.S. PATENT DOCUMENTS

| | | | |
|---|---|---|---|
| 3,496,461 A * | 2/1970 | Sessler et al. | 324/711 |
| 3,676,775 A | 7/1972 | Dupnock et al. | |
| 4,482,623 A * | 11/1984 | Tabaru et al. | 324/158.1 |
| 4,922,182 A | 5/1990 | Cox | |
| 4,989,154 A | 1/1991 | Yamashita et al. | |
| 5,280,263 A * | 1/1994 | Sugaya | 338/22 R |
| 5,303,164 A | 4/1994 | Masson et al. | |
| 5,700,617 A * | 12/1997 | Takiguchi et al. | 430/108.3 |
| 6,395,149 B1 * | 5/2002 | Palmgren | 204/192.29 |
| 6,395,809 B1 * | 5/2002 | Hayashi et al. | 524/89 |
| 6,780,388 B2 * | 8/2004 | Masuko et al. | 423/449.1 |
| 2004/0179871 A1 * | 9/2004 | Fukuda | 399/302 |
| 2006/0073335 A1 * | 4/2006 | Oyamada et al. | 428/403 |

OTHER PUBLICATIONS

Monroe Electronics, Resistance/Resistivity Meters, http://www.monroe-electronics.com.

* cited by examiner

*Primary Examiner*—Timothy J Dole
(74) *Attorney, Agent, or Firm*—TraskBritt (57) ABSTRACT

A device for measuring the volume resistivity of materials and method of measuring are disclosed. The device for measuring has a receptacle of a known volume in which fluid materials, for example powdered or granular materials which may assume the shape of the receptacle, may be placed. The receptacle may have an insulating body and electrodes in the form of conductive end caps on either longitudinal end of the body. The resistance across the device, between the electrodes, may be measured. The volume resistivity of the fluid materials may be determined using the known volume of the receptacle and the resistance.

21 Claims, 5 Drawing Sheets

METHODS AND DEVICES FOR MEASURING VOLUME RESISTIVITY

This invention was made with Government support under Subcontract No. PA01V1401N to Strategic Systems Programs, Prime Contract No. N00030-01-C-0100. The Government has certain rights in this invention.

BACKGROUND OF THE INVENTION

1. Field of the Invention

The field of the invention includes the resistivity of materials, and, more specifically, methods and devices for measuring the volume resistivity of fluid materials, such as a powder. The volume resistivity of energetic materials may be measured using the device and methods of the present invention.

2. State of the Art

Volume resistivity is the ratio of a dc voltage drop per unit thickness to the amount of current per unit area passing through a material. Volume resistivity indicates how readily a material conducts electricity through the material. The volume resistivity may also be useful to examine physical characteristics of materials such as electrostatic decay and thermal characteristics, for example, heating. Petrochemical, grain, and semiconductor industries rely on knowledge of the volume resistivity of energetic materials to prevent product and personnel loss.

One example of a conventional device for measuring resistivity is described in U.S. Pat. No. 4,922,182 to Cox. The device is capacitively coupled to a material under test. The tested material may include two outer layers and a solid, conductive buried layer. Pickup and driven electrodes are capacitively coupled at different locations to the buried layer. A frequency may be generated which resonates the capacitively coupled pickup and driven electrodes with an inductor. The voltage output of this series resonant circuit may be measured, and the resistivity of the buried layer may be determined using Ohm's law.

The pickup and driven electrodes of this conventional device are coupled to capacitive plates integral to the conductive buried layer. However, a fluid material, one which flows and conforms to the shape of a container, such as a powdered or granular material, cannot have an integral capacitive plate. Therefore, the resistivity of a fluid material cannot be measured with this conventional device.

Energetic materials are materials that react chemically to release energy. Explosives, pyrotechnics and propellants are examples of energetic materials. An energetic material may be initiated to undergo rapid, self-propagating decomposition that results in the formation of more stable material, the production of heat, or the development of a sudden pressure effect through the action of heat on produced or adjacent gases. Energetic materials are especially vulnerable to initiation when subjected to an elevated temperature. Energetic materials may also be initiated by mechanical work through friction, impact, or electricity. Energetic materials may be used, for example, as explosives in demolition, welding, detonating, cutting charges and munition fillings, as propellants for guns and rockets, as gas generators or as pyrotechnics. Energetic materials are often used in fluid, i.e., powdered or granular, form.

Therefore, there is a need for a device for measuring volume resistivity of a fluid material. There is additional need for a device for measuring volume resistivity of a energetic material, particularly in a fluid form.

BRIEF SUMMARY OF THE INVENTION

In one embodiment, a device for measuring the volume resistivity of a material comprises a body having a first end, a second end, and an opening therethrough configured for receiving a material to be measured, a first end cap attachable to the first end of the body, a second end cap attachable to the second end of the body, and a resistance measuring device configured for electrical connection with the first end cap and the second end cap. The opening may be substantially cylindrical, and configured for receiving a fluid material, for example, a powdered material. The first end cap and the second end cap may each have a blind hole on an exterior surface thereof, and the resistance measuring device may be operably coupled to a first contact member configured for insertion into the blind hole of the first end cap and a second contact member configured for insertion into the blind hole of the second end cap to establish electrical communication between the end caps and the resistance measuring device.

The opening through the body may have a cross-sectional area and a height, and the area divided by the height, for example, may be between about 1.95 cm. and about 2.05 cm. The body may be formed of an insulating material, for example, polytetrafluoroethylene (PTFE, marketed as TEFLON®), polymer, or nylon. The first end cap and the second end cap are formed, at least in part, of a conductive material.

Another embodiment of a device for measuring volume resistivity includes a receptacle of a known volume for receiving a material to be measured. The receptacle may be bounded by an inside wall of a substantially cylindrical body comprising an insulating material, a central portion of a first end cap comprising a conductive material, and a central portion of a second end cap comprising a conductive material. A resistance measuring device may be configured for electrical connection with the first end cap and the second end cap. The inside wall of the receptacle, the central portion of the first end cap, and the central portion of the second end cap may all have a substantially similar diametrical dimension. The first end cap and the second end cap may be configured to be force fit to the substantially cylindrical body with the central portion of the first end cap and the central portion of the second end cap received within an opening through the substantially cylindrical body defined by, or in communication with, the receptacle. The insulating material of the substantially cylindrical body may be, for example, PTFE, polymer, or nylon.

A method for measuring volume resistivity includes providing a body having a first end and a second end, and an opening having a known volume extending therethrough, attaching a first end cap to the first end of the body, substantially filling the opening with a material to be measured, attaching a second end cap to the second end of the body, electrically coupling a measuring device to the first end cap and the second end cap, measuring a resistance to current flow between the first end cap and the second end cap using the measuring device, and determining the volume resistivity using the resistance measurement and the known volume. The body may comprise a substantially annular body of an insulating material, and the first and second end caps may be formed, at least in part, of a conductive material.

The material to be measured may be contacted with a portion of the first end cap and a portion of the second end cap, for example, contacting the material to be measured with a portion of the first end cap and a portion of the second end cap, each portion having an area substantially equal to a cross-sectional area of the opening.

The volume resistivity may be determined according to the following mathematical relationship:

$$\rho = \frac{\pi r^2}{h} R,$$

wherein ρ represents the resistivity, $\pi r^2$ represents the opening area, h represents the opening height, and R represents the resistance in ohms. The interior height and diameter of the device may be configured such that the volume resistivity may be determined according to the mathematical relationship ρ=2R.

Other aspects and advantages will become apparent from the following detailed description, taken in conjunction with the accompanying figures.

BRIEF DESCRIPTION OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION

Figure 1:
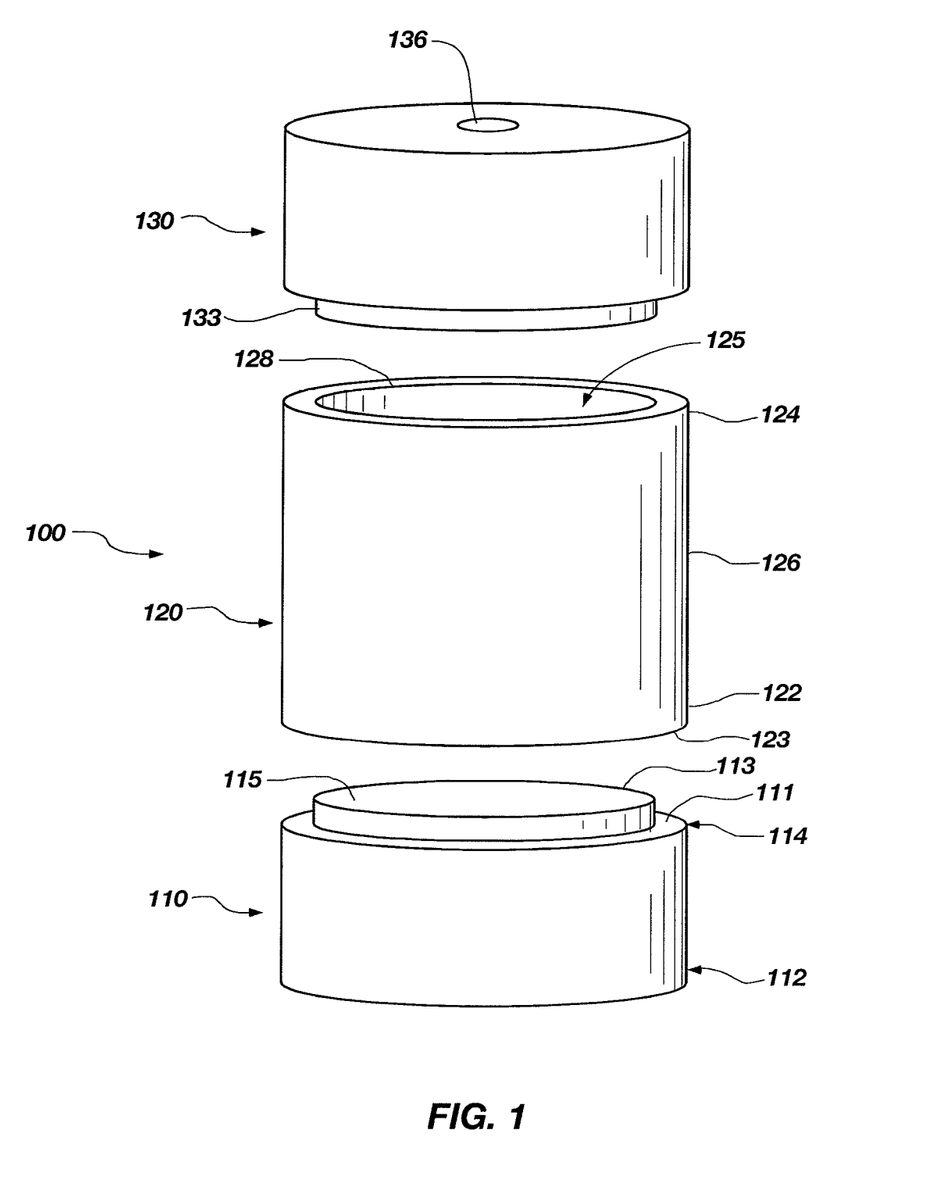
FIG. 1 is an illustration of a measuring device of the present invention.

FIG. 1 depicts an embodiment of a measuring device 100 of the present invention. The measuring device 100 includes a body 120, a first end cap 110 and a second end cap 130. The body 120 may be annular and substantially cylindrical, with an opening 125 therethrough. The body 120 comprises a first longitudinal end 122 and a second longitudinal end 124. The body 120 may further comprise an outside facing surface 126 and an inside facing surface 128. The body 120 may be formed of a non-conductive material, for example, polytetrafluoroethylene (PTFE, marketed as TEFLON®), polymer, or nylon.

The first end cap 110 includes a first longitudinal end 112 and a second longitudinal end 114. On the second longitudinal end 114, a rim of the first end cap 110 forms a shoulder 111. A central portion 113 of the second longitudinal end 114 of the first end cap 110 protrudes from the shoulder 111. The first end cap 110 may be attached to the first longitudinal end 122 of the body 120. The central portion 113 of the first end cap may have an outside diametrical dimension just smaller than the diametrical dimension of the inside facing surface 128 of the body 120. The central portion 113 may be inserted into the opening 125 of the body 120 until a first longitudinal end surface 123 of the body 120 abuts the shoulder 111 of the first end cap 110. The first end cap 110 may thus be force fitted to the body 120.

The outside diametrical dimension of the first end cap 110 and the second end cap 130 may be substantially similar to the diametrical dimension of the outside facing surface 126 of the body 120. Thus, with the first end cap 110 and the second end cap 130 attached to the body 120, a single cylinder is formed, with a substantially uniform outside diametrical dimension.

Other methods of attaching the end caps 110, 130 are within the scope of the present invention. For example, a portion of the inside surface 128 of the body 120 may be threaded to mate with threads on an outside surface of the central portion 113 of the end caps 110, 130. As another example, the end caps 110, 130 may have a flange for fitting about a portion of the outside surface 126 of the body 110. Non-threaded attachment methods may be useful when working with energetic materials, as there is a risk that some of the energetic material may be caught in the threads and subjected to increased pressure.

Figure 2A:
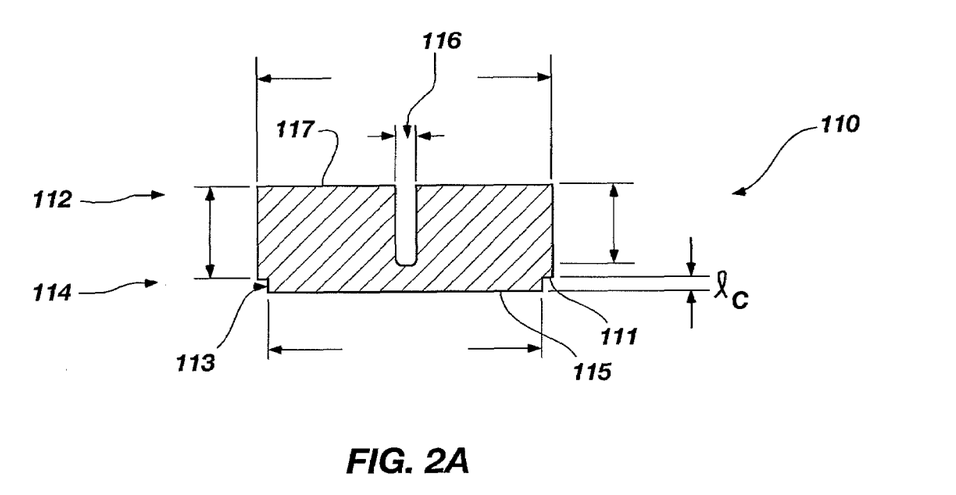
FIG. 2A is cross-sectional view of an end cap of the present invention.
Figure 2B:
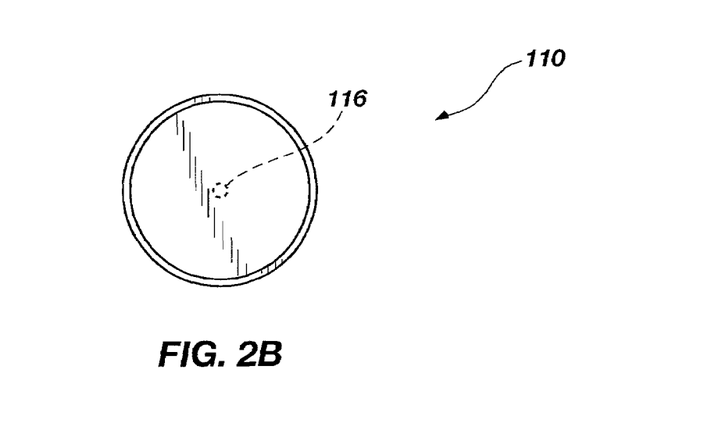
FIG. 2B is a top view of an end cap of the present invention.
Figure 5:
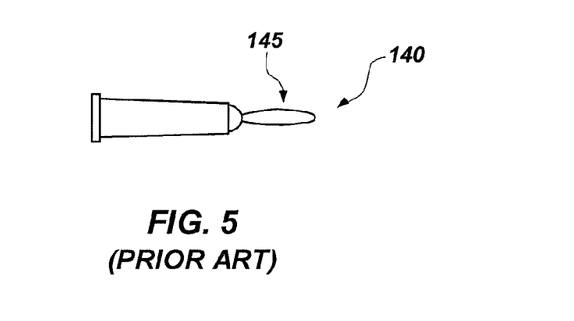
FIG. 5 is an illustration of a banana plug.

Turning to FIGS. 2A and 2B, a cross-sectional view and a top view of the first end cap 110 are shown. The second end cap 130 may be substantially similar to the first end cap 110, with substantially similar features and dimensions. The end caps 110, 130 may comprise a conductive material, for example, a metal such as stainless steel or aluminum. The first longitudinal end 112 has a first surface 117 with a blind hole 116 therein. The blind hole 116 may be substantially centrally located in the first surface 117, and extend longitudinally within the first end cap 110. The blind hole 116 does not extend all the way through the end cap 110, to the opposing, second side 115. The blind hole 116 may be sized and shaped to receive a contact portion 145 of a contact member 140 therein. One example of a suitable contact member 140 is a conventional banana plug, depicted in FIG. 5. Inserting the contact member 140 into the blind hole 116 is one method of providing an electrical connection to the end cap 110. Other methods of establishing an electrical connection to the end cap 110 are within the scope of the present invention.

It is preferred to clean all of the surfaces of the measuring device 100 before use. One example of a suitable cleaning method is to use a solvent, for example, acetone. Cleaning the surfaces will remove other materials which may be on inside surfaces of measuring device 100 and contaminate the sample to be tested. Contaminants on an outside surface may provide a more conductive path across the device during testing, and provide misleading testing results.

The volume resistivity of a material may be measured using the measuring device 100. One end cap, for example, the first end cap 110 may be attached to the body 120. Optionally, the first end cap 110 may be permanently attached to or formed as part of the body 120, and the opening 125 through the body 120 may be accessed at the second longitudinal end 124 of the body 120. The opening 125 forms a receptacle, and may be filled with the material to be tested. The material to be tested may be in a fluid form, for example, powdered or granular, so that the material may fill and conform to the shape of the opening 125. It will be understood by one skilled in the art that filling the opening means filling the opening such that room remains for another end cap, for example, the second end cap 130 to be attached. The central portion 133 of the second end cap 130 may be disposed within the opening 125, if the method of attachment of the second end cap 130 includes a central portion 133 to fit within the opening 125. Other suitable methods, as previously mentioned, of attaching the second end cap 130 which enable at least a portion of the second end cap 130 to contact the material filling the opening 125 are within the scope of the present invention. The material to be tested fills the opening 125, and contacts the conductive material of the attached end caps 110, 130. The material to be tested is thus enclosed in a receptacle of a known volume, and the volume of the material to be tested is known.

Figure 4A:
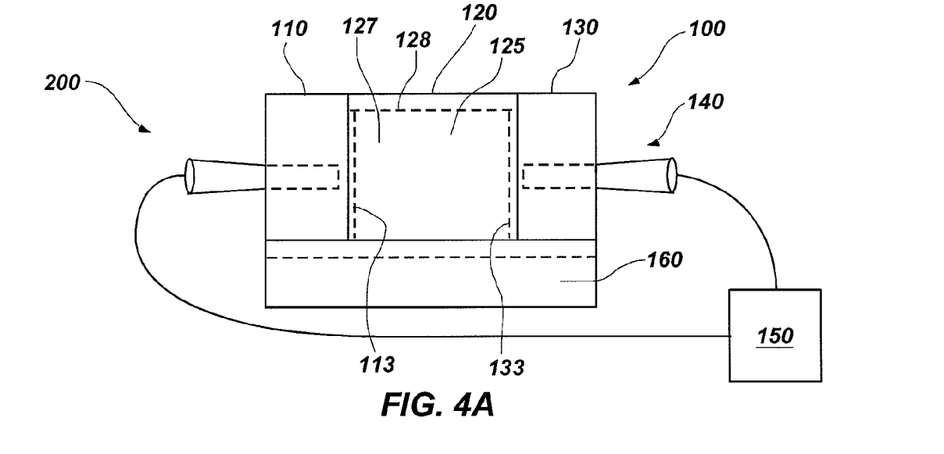
FIG. 4A is a schematic illustration of a measuring system of the present invention.
Figure 4B:
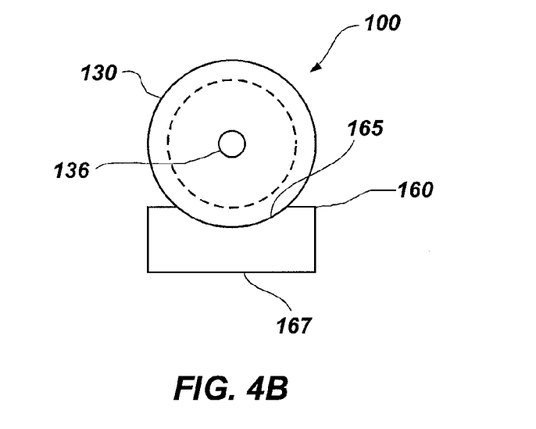
FIG. 4B is a side view of a measuring device of the present invention.

A measuring system 200 for determining volume resistivity is depicted in FIG. 4A. The measuring device 100 with end caps 110, 130 attached to the body 120 is shown. The measuring device 100 may rest on a holder 160. The holder 160 may be cradle-shaped, providing an upper, curved surface 165 for receiving the measuring device 100, and a substantially flat, bottom surface 167 for stably placing the measuring device 100. The holder 160 may be formed of an insulating material, for example, PTFE, polymer, or nylon, to prevent an undesired conductive path between the end caps 110 and 130. A receptacle 127 of a known volume is formed within the measuring device 100, bounded by the inside facing surface 128 of the body 120 and the central portions 113, 133 of the end caps 110, 130.

Electrical connection between the end caps 110, 130 and a resistance measuring device 150, for example, an ohm meter, may be established by connecting a contact member 140 (see also FIG. 5) into each blind holes 116, 136. The contact members 140 may be in electrical communication with the resistance measuring device 150. The end caps 110, 130 may act as electrodes, providing a conductor through which electrical current from the resistance measuring device 150 may pass to the material to be tested within the measuring device 100. The resistance may thus be measured with the resistance measuring device.

The body 120 comprises a non-conductive, or insulating material. Thus, as a voltage is applied across the end caps 110, 130 by the resistance measuring device 150, the material filling the receptacle 127 may conduct the current. The resistance measuring device 150 may thus measure the resistance of the material to be tested.

Volume resistivity of a piece of material having known physical dimensions and a known resistance may be calculated using the equation:

$$\rho = \frac{A}{t}R$$

Where
ρ=resistivity;
A=material area;
t=material thickness; and
R=resistance in ohms, measured across the thickness of the material.

The volume resistivity of a material being tested in the measuring device 100 and filling the opening 125 may be calculated using the equation:

$$\rho = \frac{\pi r^2}{h}R \quad \text{[Equation 1]}$$

Where
ρ=resistivity;
πr²=opening area;
r=opening radius;
h=opening height; and
R=resistance in ohms.

It may be desirable for the dimensions of the measuring device 100 to be configured so that πr²/h is substantially equal to a whole number for ease of calculation of the volume resistivity. For example, the inside diameter $d_i$ of the body 120, as shown on FIG. 3B, may be 2.55 cm, and the height h of the body 120 may be 3.23 cm. The central portion 113, 133 of the end caps 110, 130 each may protrude a length $\ell_c$ 0.32 cm (FIG. 2A) within the opening 125 when attached to the body 120. Thus the device cavity radius is 1.28 cm, and the device cavity height is 2.59 cm. This yields a multiplication factor of 1.97 cm, which, when rounded to 2, is a multiplication easy to utilize in the field. A multiplication factor between about 1.95 cm. and about 2.05 cm may be useful. Other sizes of the measuring device 100 may provide a device cavity also having a multiplication factor of two. For example, the device radius and the device height may both be larger, or the device radius and the device height may both be smaller. It will be understood by one skilled in the art that a multiplication factor of about 2 is not necessary, but may be a useful feature.

The end caps 110, 130 act as electrodes, and contact the material to be tested. The contact area is equal to the area of the protruding central portion of the end caps, which is also equal to the cross-sectional area of the material under test. End caps having conductive portions which do not contact the entire cross-sectional area of the material to be tested are within the scope of the present invention, however, the formula for determining the volume resistivity must be adjusted accordingly.

The body 120 comprises a non-conductive, or insulating material. Thus, as a voltage is applied across the end caps 110, 130 by the resistance measuring device 150, the material filling the receptacle 127 may conduct the current. Thus, the resistance measuring device 150 may measure the resistance of the material to be tested.

Figure 6:
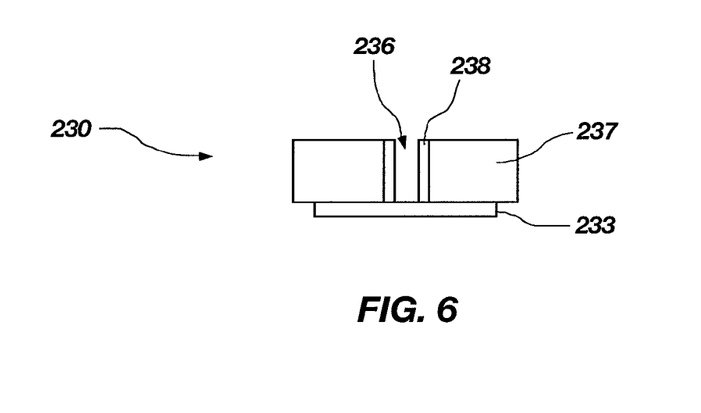
FIG. 6 is an illustration of another embodiment of an end cap of the present invention.

FIG. 6 depicts another embodiment of an end cap 230 of the present invention. The end cap 230 may be substituted for the first end cap 110, the second end cap 130, or both end caps 110, 130 with the measuring device 100 of FIG. 1. The end cap 230 may comprise an annular body 237 which may comprise an electrically insulating material. An opening 236 through the annular body 237 may be lined with a conductive material 238. The conductive material 238 may be in electrical communication with a central, protruding portion 233. The central, protruding portion 233 may comprise an electrically conductive material, and may function as an electrode of a measuring device. The central protruding portion 233 may be fitted within the opening 125 of the body 120 to provide a force-fit of the end cap 230 on the body 120.

Figure 7:
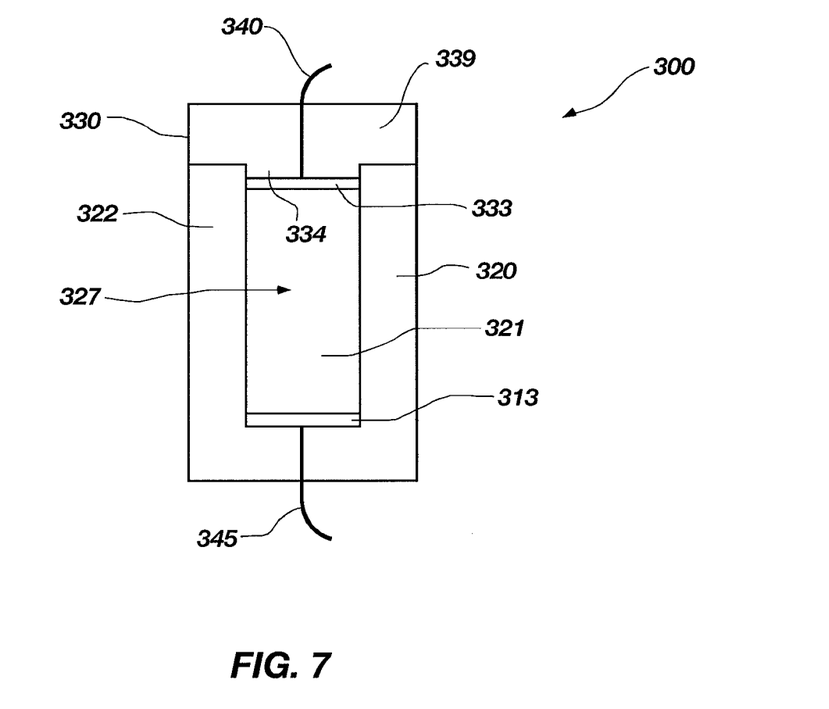
FIG. 7 depicts another embodiment of a measuring device of the present invention.

Another embodiment of a measuring device 300 is shown in FIG. 7. The measuring device 300 includes a body 320 and an end cap 330. The body 320 may comprise a substantially cylindrical body with a cavity 327 therein. A bottom surface of the cavity may comprise a conductive plate 313. The sidewalls 322 of the body 320 may comprise an electrical insulating material. The end cap 330 comprises an insulating plate 339 with a protruding central portion 334. The protruding central portion 334 may be covered with a conductive cap 333, with a substantially similar diametrical dimension to the cavity 327. The end cap 330 may be force-fit on the body 320 with the protruding central portion 334 and the conductive cap 333 extending within the cavity 327. With the end cap 330 attached to the body 320, an internal chamber or receptacle 321 is defined. The internal chamber 321 is bounded by the conductive cap 333 and the conductive plate 313, which define the longitudinal ends thereof, and the non-conductive sidewalls 322.

A conductive element 340 may be in electrical communication with the conductive cap 333, and pass through the insulating plate 339 of the end cap 330 and extend therefrom for connection to a resistance measuring device. Likewise, a conductive element 345 may be in electrical communication with the conductive plate 313. and pass through the body 320, and extend therefrom for connection to the resistance measuring device. The measuring device 300 may be used to measure resistivity of a fluid material deposited within the cavity 327 of the body 320, and sealed therein with the end cap 330. The fluid material thus fills the internal chamber 321, and is contacted by two electrodes, the conductive cap 333 and the conductive plate 313.

The measuring device of the present invention may also be useful for comparative analysis of different materials. Samples may be taken from different batches of materials, and may be tested to compare with the test results of other batches. While using a measuring device or multiple measuring devices all having uniform receptacle sizes, the sample size will be uniform and repeatable. Thus the resistivity of different batches may be compared, even by merely comparing the resistance measurement of different samples, without further calculation.

Although the foregoing description contains many specifics, these should not be construed as limiting the scope of the present invention, but merely as providing illustrations of some exemplary embodiments. Similarly, other embodiments of the invention may be devised that do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

The invention claimed is:

1. A device for measuring volume resistivity, comprising:
a structure defining an internal chamber configured for receiving a material to be measured, and having a first electrode coupled at a first end thereof and a second electrode coupled at an opposing end thereof, wherein each of the first electrode and the second electrode includes a central portion extending into the internal chamber and a shoulder extending therefrom and abutting an external surface of an end of the internal chamber adjacent thereto to fix a volume of the internal chamber; and
a resistance measuring device electrically connected to the first electrode and the second electrode, for measuring the resistance of the material, wherein volume resistivity is determined using the resistance measurement and the fixed volume.

2. The device of claim 1, wherein the internal chamber is substantially cylindrical and is configured for receiving a fluid material.

3. The device of claim 1, wherein the internal chamber is configured for receiving a powdered material.

4. The device of claim 1, wherein the internal chamber has an area and a height, and the area divided by the height is between about 1.95 cm. and about 2.05 cm.

5. The device of claim 1, wherein the structure comprises:
a body having a first end, a second end, and an opening partially defining the internal chamber;
a first end cap attachable to the first end of the body, and comprising the first electrode; and
a second end cap attachable to the second end of the body, and comprising the second electrode.

6. The device of claim 5, wherein the first end cap and the second end cap each have a blind hole therein.

7. The device of claim 6, wherein the resistance measuring device includes a first contact member configured for insertion into the blind hole of the first end cap and a second contact member configured for insertion into the blind hole of the second end cap.

8. The device of claim 5, wherein the body comprises an insulating material.

9. The device of claim 8, wherein the body comprises one of polytetrafluoroethylene, polymer, and nylon.

10. A device for measuring volume resistivity, comprising:
a receptacle configured for receiving a material to be measured and having a fixed volume defined by an inside wall of a substantially cylindrical body comprising an insulating material, a central portion of a first end cap comprising a conductive material secured to a first end of the cylindrical body, and a central portion of a second end cap comprising a conductive material secured to a second end of the cylindrical body, wherein each of the first end cap and the second end cap includes a shoulder abutting an external surface of an associated end of the cylindrical body; and
a resistance measuring device electrically connected to the conductive material of the first end cap and the conductive material of the second end cap, for measuring the resistance of the material, wherein volume resistivity is determined using the resistance measurement and the fixed volume.

11. The device of claim 10, wherein the inside wall has a diametrical dimension, and the central portion of the first end cap has a diametrical dimension, and the central portion of the second end cap has a diametrical dimension, and the diametrical dimension of the inside wall, the central portion of the first end cap, and the central portion of the second end cap are substantially similar.

12. The device of claim 10, wherein the first end cap and the second end cap are configured to be force fit to the substantially cylindrical body with the central portion of the first end cap and the central portion of the second end cap receivable within an opening through the substantially cylindrical body.

13. The device of claim 10, wherein the insulating material of the substantially cylindrical body comprises one of polytetrafluoroethylene, polymer, and nylon.

14. A method for measuring volume resistivity, comprising:
providing a body having a first end and a second end, and an opening having a known volume extending therethrough;
attaching a first end cap to the first end of the body and abutting a shoulder of the first end cap against an external surface of the first end of the body;
substantially filling the opening with a material to be measured;
attaching a second end cap to the second end of the body and abutting a shoulder of the second end cap against an external surface of the second end of the body to fix a volume of the opening between the first end cap and the second end cap;
electrically coupling a measuring device to the first end cap and the second end cap; measuring the resistance between the first end cap and the second end cap using the measuring device; and determining the volume resistivity using the resistance measurement and the known volume.

15. The method of claim 14, wherein providing a body comprises providing a substantially annular body comprising an insulating material.

16. The method of claim 14, wherein attaching the first end cap comprises attaching the first end cap comprising a conductive material, and attaching the second end cap comprises attaching the second end cap comprising a conductive material.

17. The method of claim 14, wherein determining the volume resistivity is executed according to the following mathematical relationship:

$$\rho = \frac{\pi r^2}{h} R,$$

wherein p=resistivity; r=opening radius; h=opening height; and R=measured resistance.

18. The method of claim 17, wherein determining the volume resistivity is executed according to the following mathematical relationship:

p=2R.

19. The method of claim 14, wherein attaching the second end cap comprises contacting the material to be measured with a portion of the second end cap.

20. The method of claim 19, wherein attaching the second end cap comprises contacting the material to be measured with the portion of the second end cap having an area substantially equal to a cross-sectional area of the opening.

21. The method of claim 14, wherein substantially filling the opening with a material to be measured comprises substantially filling the opening with an energetic material.

* * * * *

UNITED STATES PATENT AND TRADEMARK OFFICE
CERTIFICATE OF CORRECTION

| | | |
|---|---|---|
| PATENT NO. | : 7,609,073 B2 | Page 1 of 1 |
| APPLICATION NO. | : 11/438084 | |
| DATED | : October 27, 2009 | |
| INVENTOR(S) | : Jared K. Olson, Ronald G. Mellus and Travis A. Bodrero | |

It is certified that error appears in the above-identified patent and that said Letters Patent is hereby corrected as shown below:

In the specification:

COLUMN 1, LINE 3, after "VOLUME RESISTIVITY" and before "This invention" insert and center --STATEMENT REGARDING FEDERALLY SPONSORED RESEARCH OR DEVELOPMENT--

COLUMN 1, LINE 66, change "a energetic" to --an energetic--

COLUMN 3, LINE 66, change "cap" to --cap 110--

COLUMN 5, LINES 7-9, after "is known." and before "A measuring system" insert paragraph --Some materials to be tested, particularly energetic materials, may be hazardous when under pressure. An operator must be cautious to ensure that when attaching the second end cap 130, pressure applied to the material to be tested does not reach a dangerous level.--

COLUMN 5, LINE 26, change "holes" to --hole--

COLUMN 5, LINE 33, change "device." to --device 150.--

Figure 3A:
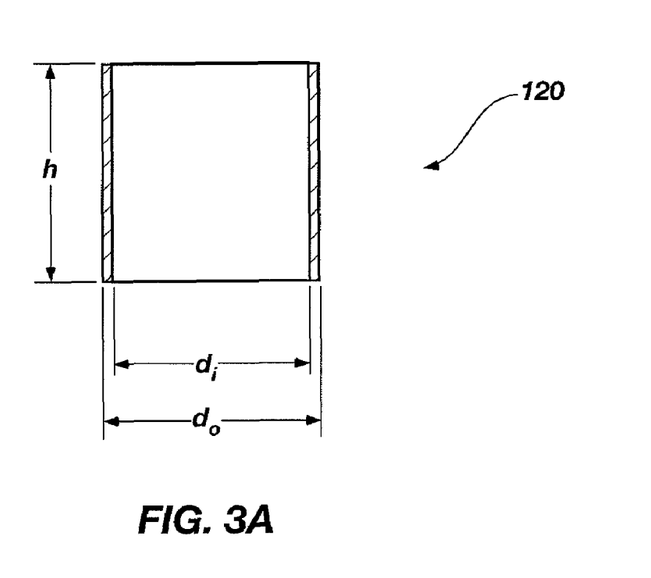
FIG. 3A is cross-sectional view of a body of a measuring device of the present invention.
Figure 3B:
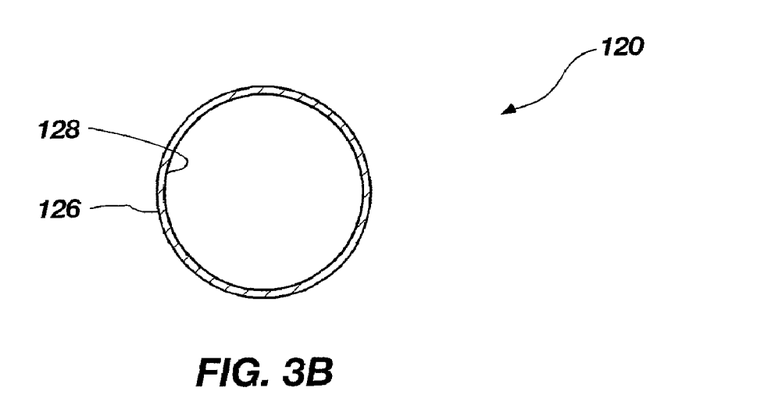
FIG. 3B is a top view of a body of a measuring device of the present invention.

COLUMN 6, LINE 7, change "on FIG. 3B," to --in FIG. 3A,--

COLUMN 6, LINE 9, change "length $\ell_c$0.32 cm" to --length $\ell_c$ 0.32 cm--

COLUMN 6, LINE 16, change "cm. and" to --cm and--

COLUMN 6, LINE 25, change "portion of the end caps," to --portion 113, 133 of the end caps 110, 130,--

COLUMN 7, LINE 9, change "313. and" to --313, and--

In the claims:

CLAIM 4, COLUMN 7, LINE 64, change "cm. and" to --cm and--
CLAIM 10, COLUMN 8, LINE 22, change "the cylindrical" to --the substantially cylindrical--
CLAIM 10, COLUMN 8, LINE 24, change "the cylindrical" to --the substantially cylindrical--
CLAIM 17, COLUMN 10, LINE 1, change "p=resistivity;" to --$\rho$=resistivity;--
CLAIM 18, COLUMN 10, LINE 6, change "p=2R." to --$\rho$=2R.--

Signed and Sealed this
Twenty-first Day of May, 2013

Teresa Stanek Rea
*Acting Director of the United States Patent and Trademark Office*